US012599410B2

(12) United States Patent
Ziran et al.

(10) Patent No.: US 12,599,410 B2
(45) Date of Patent: Apr. 14, 2026

(54) MULTI-CLAMP APPARATUS FOR EXTERNAL BONE FIXATOR

(71) Applicant: ADVANCED TRAUMA SOLUTIONS, LLC, Decatur, GA (US)

(72) Inventors: Bruce H. Ziran, Decatur, GA (US); Patrick Kelly Capeheart, Dahlonega, GA (US)

(73) Assignee: ADVANCED TRAUMA SOLUTIONS, LLC, Decatur, GA (US)

( * ) Notice: Subject to any disclaimer, the term of this patent is extended or adjusted under 35 U.S.C. 154(b) by 44 days.

(21) Appl. No.: 18/943,046

(22) Filed: Nov. 11, 2024

(65) Prior Publication Data

US 2025/0064483 A1 Feb. 27, 2025

Related U.S. Application Data

(60) Continuation-in-part of application No. 18/120,042, filed on Mar. 10, 2023, now Pat. No. 12,496,097, which is a division of application No. 17/524,285, filed on Nov. 11, 2021, now Pat. No. 11,660,122.

(60) Provisional application No. 63/163,146, filed on Mar. 19, 2021.

(51) Int. Cl.
*A61B 17/64* (2006.01)

(52) U.S. Cl.
CPC ........ *A61B 17/6458* (2013.01); *A61B 17/645* (2013.01)

(58) Field of Classification Search
CPC ..... A61B 17/60; A61B 17/64; A61B 17/6416; A61B 17/6433; A61B 17/6441; A61B 17/6458; A61B 17/66; A61B 17/645
See application file for complete search history.

(56) References Cited

U.S. PATENT DOCUMENTS

| | | | | |
|---|---|---|---|---|
| 3,055,398 A * | 9/1962 | Tunnessen | ............ | F28F 9/0132 |
| | | | | 206/443 |
| 4,620,533 A * | 11/1986 | Mears | .................. | A61B 17/645 |
| | | | | 606/54 |
| 5,947,671 A * | 9/1999 | Kanaan | .................... | G05G 1/10 |
| | | | | 74/555 |
| 9,155,560 B2 * | 10/2015 | Mingozzi | ........... | A61B 17/6416 |
| 10,172,646 B2 * | 1/2019 | Slagle | .................... | A61B 17/60 |
| 10,722,268 B2 * | 7/2020 | Muniz | ................ | A61B 17/6416 |

(Continued)

*Primary Examiner* — Ellen C Hammond
(74) *Attorney, Agent, or Firm* — Thomas I Horstemeyer, LLP

(57) ABSTRACT

Embodiments of a multi-clamp apparatus for an orthopedic exterior fixator are disclosed. One embodiment of the multi-clamp apparatus has two clamp arms, each having a plurality of opposing crescentic channels that, when pressed together, are of a length, size, and shape to engage and secure a plurality of bone pins. An outrigger bar extends from each of the clamp arms for attachment of fixator components. Each clamp arm has a collapsible torque amplifying knob that can be hand operated and that causes relative movement of the two clamp arms for concurrently clamping and unclamping multiple bone pins when rotational force is applied to one or both of the knobs. The turn levers of each knob can be collapsed in a generally mating, side-by-side arrangement. The turn levers of the knobs are ergonomically designed so that the knobs can be hand operated, without tools, in the collapsed and un-collapsed configurations.

20 Claims, 8 Drawing Sheets

(56)     References Cited

U.S. PATENT DOCUMENTS

| | | | |
|---|---|---|---|
| 2006/0287652 A1* | 12/2006 | Lessig | A61B 17/6458 |
| | | | 606/54 |
| 2017/0327350 A1* | 11/2017 | Swope | B66C 1/64 |
| 2019/0110814 A1* | 4/2019 | Nemovicher | A61B 90/57 |
| 2021/0100585 A1* | 4/2021 | Kent | A61B 17/6466 |

* cited by examiner

MULTI-CLAMP APPARATUS FOR EXTERNAL BONE FIXATOR

CLAIM OF PRIORITY

This application is a continuation-in-part (CIP) of application Ser. No. 18/120,042, filed Mar. 10, 2023, which is a division of Ser. No. 17/524,285, filed Nov. 11, 2021, now U.S. Pat. No. 11,660,122, which claims the benefit of provisional application No. 63/163,146, filed Mar. 19, 2021, all of the foregoing of which are incorporated herein by reference in their entireties.

RELATED APPLICATIONS

This application is related to co-pending application "Hinge Apparatus For External Bone Fixator, application Ser. No. 18/943,039, filed on even date herewith, which is incorporated herein by reference in its entirety.

FIELD OF THE INVENTION

The embodiments of the present disclosure generally relate to the medical field of bone fractures and deformity, and more particularly, to multi-purpose external fixators that are used for stabilizing fractures in patients.

BACKGROUND OF THE INVENTION

In the medical field of orthopedics, for several years a technique has been known for stabilizing fractures by using external fixators instead of conventional plaster casts. External fixators usually comprise a plurality of threaded bone pins, or screws, normally in pairs, which are implanted in the bone fragments of the fracture in such a way that the head ends of the bone pins project from the skin of the patient. The ends are anchored to a rigid external frame which is equipped with clamps and rods, which can be orientated in such a way as to allow them to be adjusted to the position of the bone pins.

The bone pins usually have a cylindrical body, delimited on one side by a threaded end designed to be screwed into the bone fragment, and on the other side by the above-mentioned head end, which is shaped in such a way that it can be connected to a temporary grip that allows the pin to be screwed into the bone fragment. The connection between the pin and the grip is normally of the male-female type with quick coupling and release or another conventional mechanical interface.

During its application the pins are placed on opposite sides of the fracture span and connect to a clamp that allows connectivity between pins. Then the surgeon connects the pins, clamps, and a series of bars together. If necessary, the surgeon then aligns the limb for either temporary or permanent positioning. In most cases, the alignment is also to stabilize the body part to prevent further damage, and allow transport to a different level of care, or to allow the injury to evolve and ultimately allow a safer invasive procedure (damage control, often called "reduction").

Once the fracture has been reduced, the surgeon locks the joints and clamps to hold the bone fragments in the predetermined position, thus allowing the correct alignment between the bone fragments, which through the formation of "bone callus", gradually restores the lamellar bone tissue with which the bone recovers its original continuity and functionality.

The use of external fixators was extended to a vast range of orthopedic operations, such as limb lengthening, correction of bone axis rotary and angular deformities, pseudarthrosis, etc. In other words, external fixators are today used as multi-purpose orthopedic devices, both to correct deformations caused by trauma and to correct pathological deformations.

U.S. Pat. No. 9,155,560, which is incorporated herein by reference, discloses an example, among others, of a multi-purpose external fixator that has a universal clamp apparatus. The universal clamp apparatus has parallel first and second clamps, each having a pair of channels, one that is sized to receive and attach to a rod associated with a frame of the fixator and another that is sized to receive and attach to a bone pin. A collapsible handle with cam mechanism is employed to selectively either secure or unsecure the frame rod and/or bone pin in the first and second clamps. When the handle is closed, the frame rod and/or bone pin are squeezed and secured in the respective channels. A primary disadvantage of this universal clamp apparatus is that when the handle is closed, the first and second clamps have an imprecise fixed degree of tightness with respect to the rod and/or bone pin. This results in an inability to properly secure the frame rod and/or bone pin as well as readjust the squeezing tightness, when necessary. Furthermore, there is a risk that the collapsible handle could catch an object and get loosened, thereby causing the clamp to lose stability.

Other fixators have utilized a progressive tightening, usually through the use of a compressive screw design. These fixators typically require the use of a tool, such as a wrench, to tighten and loosen the clamp. In the surgical arena, the tool is often part of a "set" of instruments that requires sterilization. Without the tool, the clamp tightening can be compromised, even when provisional texturing of the clamp allows some "hand tightening". When these fixators are used in austere environments (i.e., warfare, rural and underserved areas), the tool may be lost and the utility of the fixator is compromised.

Commonly assigned U.S. Pat. No. 11,660,122, which is incorporated herein by reference, discloses a universal clamp apparatus for a bone fixation device that uses progressive tightening and that can be operated without the need for any tools. The universal clamp apparatus has at least one pin/rod clamp, but preferably two pin/rod clamps. Each clamp has seating grooves for snapping in and attaching to at least one of the following: a frame rod associated with a frame of the fixator and/or a bone pin for implantation in a bone fragment. A screw mechanism, such as a clamp screw, extends through and connects the first and second pin/rod clamps. An ergonomically designed knob having at least one collapsible or non-collapsible turn lever acts as a torque amplifier when rotated to tighten and untighten the pin/rod clamps to the frame rod and/or bone pin by movement along the clamp screw. A planar side of the pin/rod clamps that are contiguous each have radial ratchet grooves that are in mating engagement and that implement a ratcheting and securing mechanism so that the rotation of the pin/rod clamps relative to each other occurs in discrete incremental rotational steps.

SUMMARY OF THE INVENTION

Various embodiments of a multi-clamp apparatus for an orthopedic exterior fixator are disclosed.

One embodiment, among others is a multi-clamp apparatus having two clamp arms. Each clamp arm has a plurality of opposing crescentic channels that, when pressed together, are of a length, size, and shape to engage and secure a plurality of bone pins. An outrigger bar extends from each of the clamp arms for attachment of fixator components. Each clamp arm has a collapsible torque amplifying knob that is hand operated and that causes relative movement of the two clamp arms for concurrently clamping and unclamping multiple bone pins when rotational force is applied to one or both of the knobs. The turn levers of each knob can be collapsed in a side-by-side arrangement. The turn levers of the knobs are ergonomically designed to that the knobs can be hand operated, without tools, in the collapsed and un-collapsed configurations.

Other embodiments, apparatus, methods, features, and advantages of the present invention will be apparent to one with skill in the art upon examination of the following drawings and detailed description. It is intended that all such additional embodiments, apparatus, methods, features, and advantages be included within this disclosure, be within the scope of the present invention, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE
PREFERRED EMBODIMENT(S)

Figure 1:
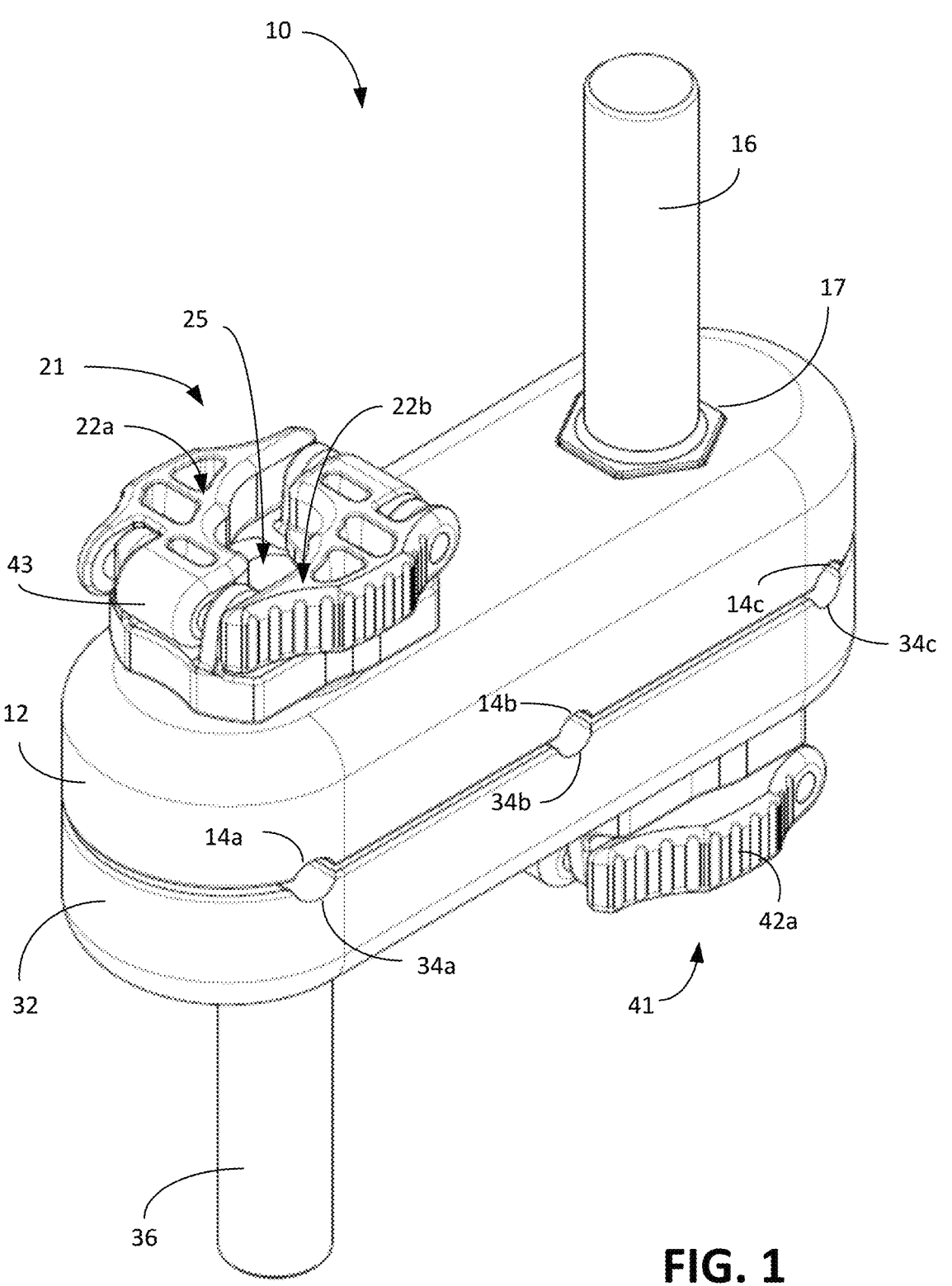
FIG. 1 is a perspective view of the multi-clamp apparatus for a bone fixation device with torque amplifying knobs in a collapsed configuration.
Figure 2:
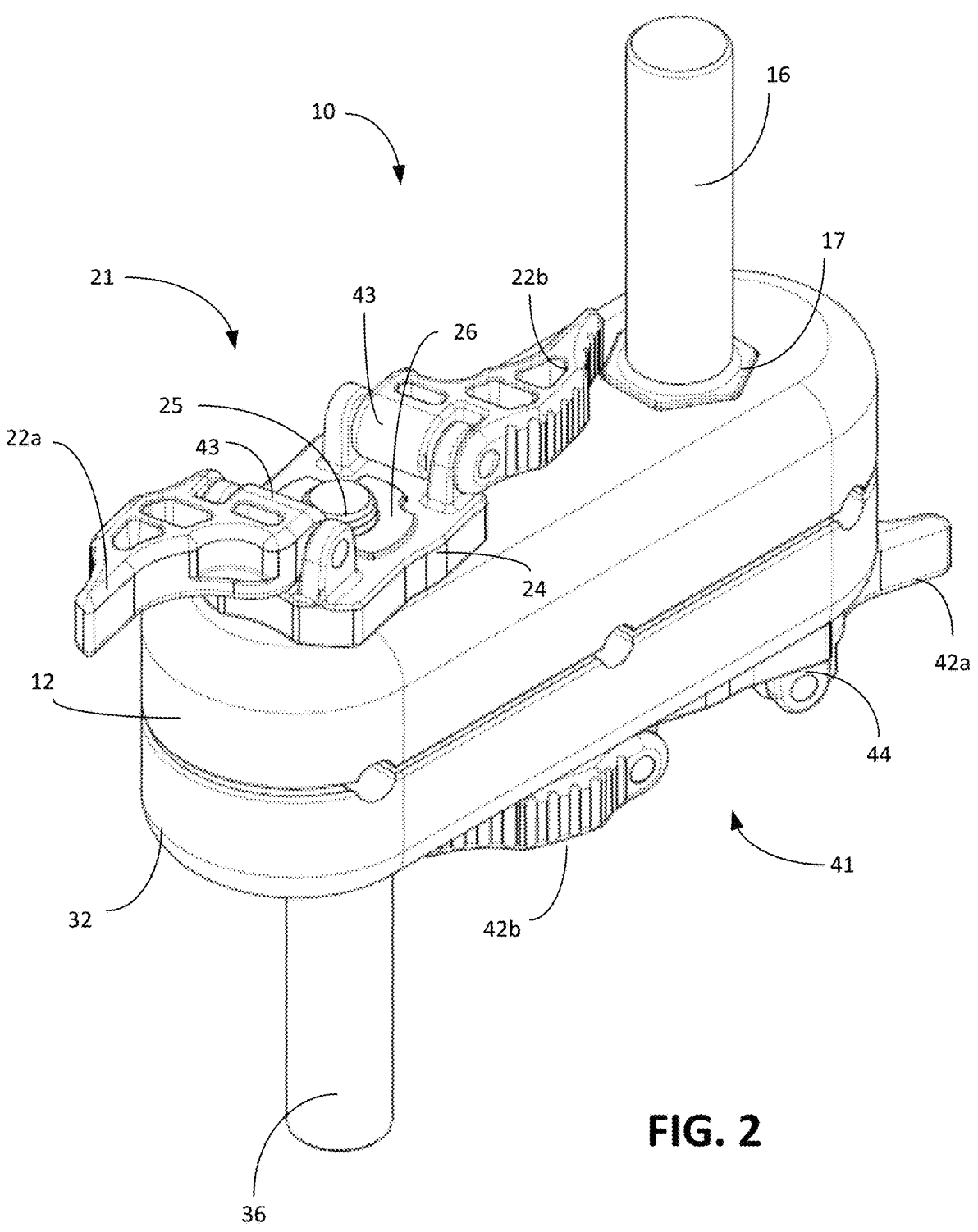
FIG. 2 is a perspective view of the multi-clamp apparatus of FIG. 1 with the torque amplifying knobs in an un-collapsed configuration.
Figure 3:
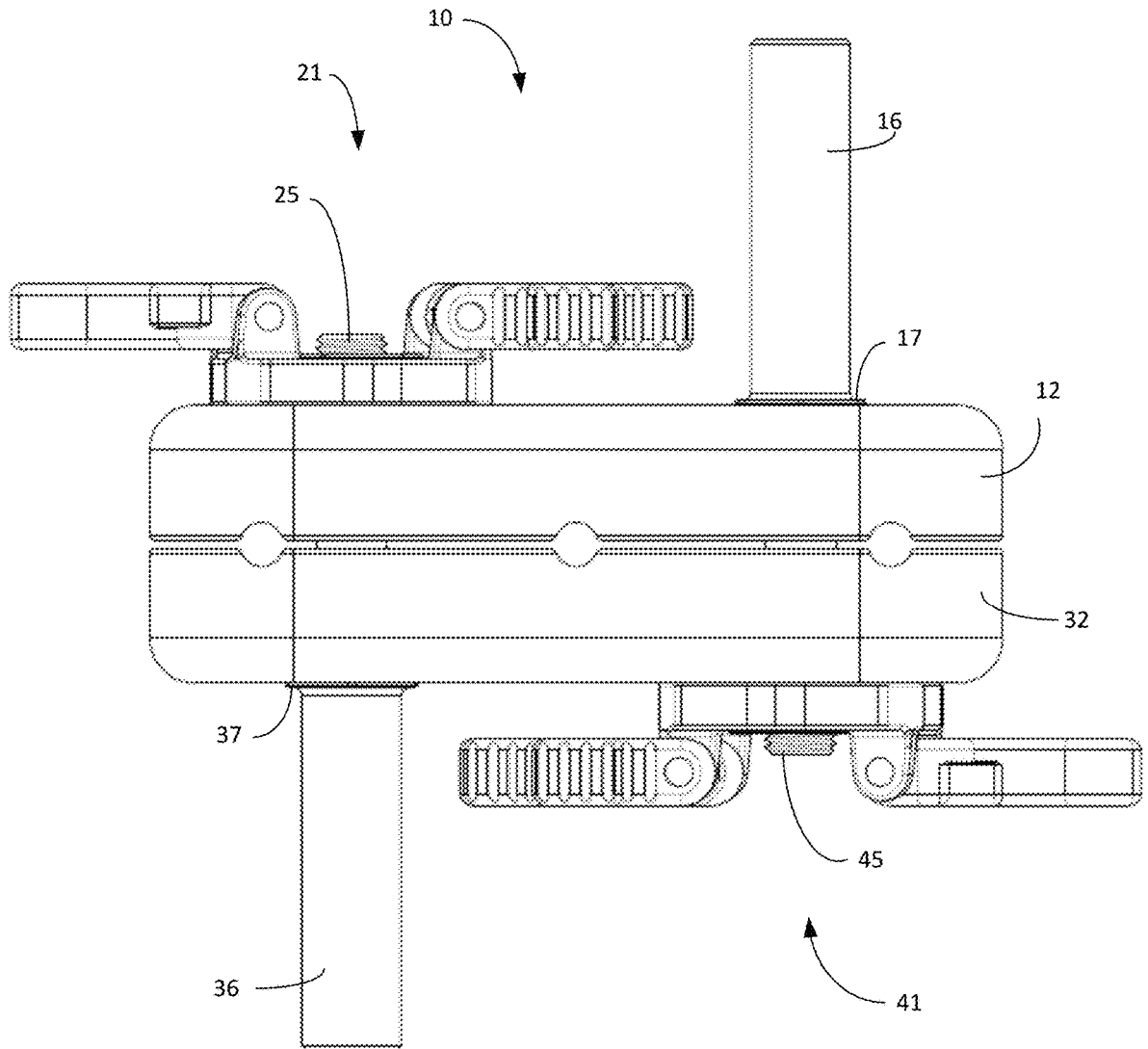
FIG. 3 is a front side view of the multi clamp apparatus of FIGS. 1 and 2.
Figure 4:
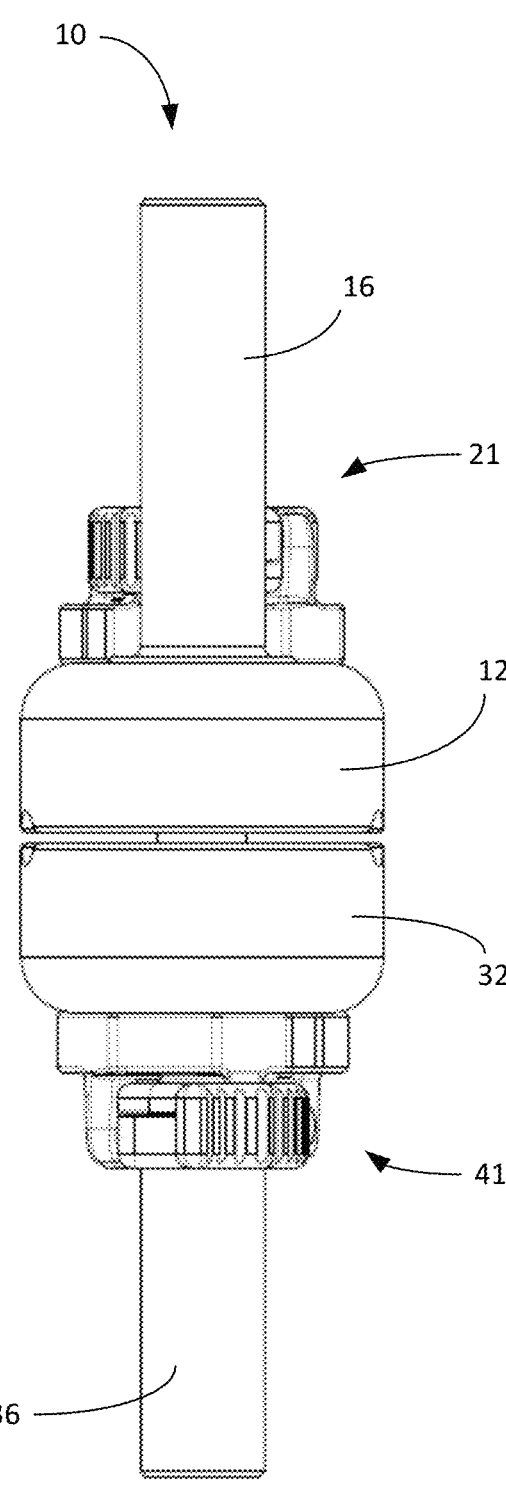
FIG. 4 is a left side view of the multi-clamp apparatus of FIGS. 1 and 2. The right side view is a mirror image of the left side view.
Figure 5:
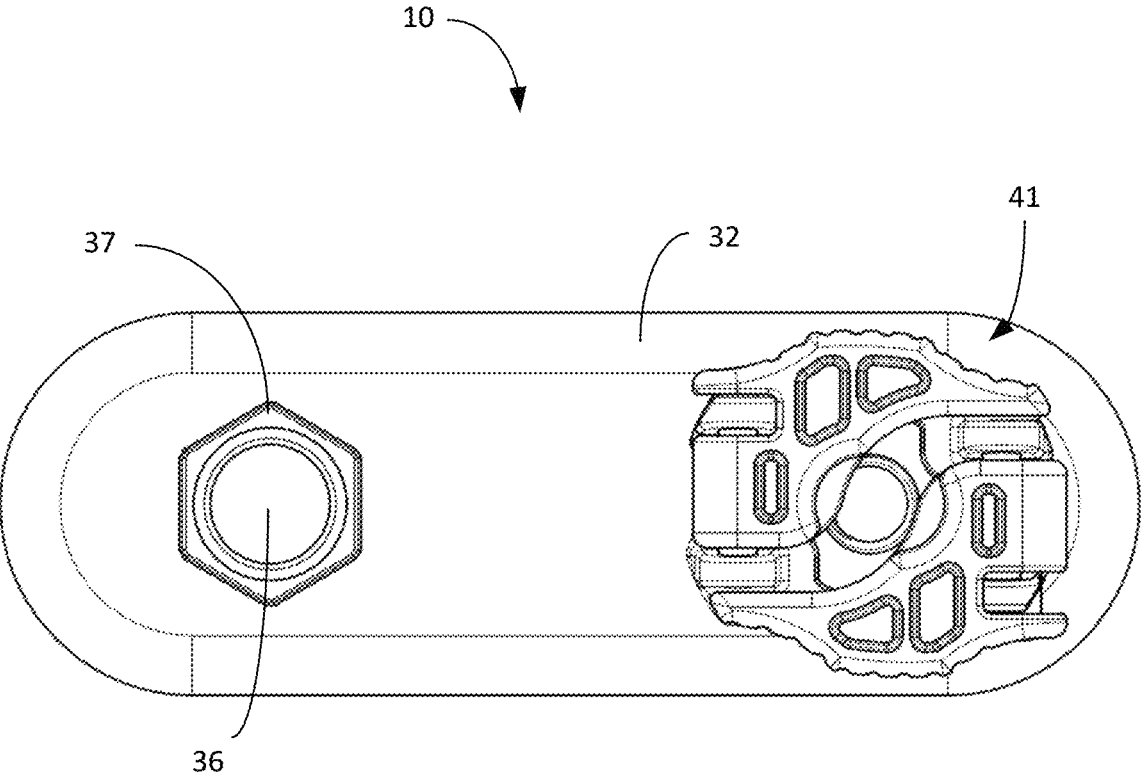
FIG. 5 is a bottom side view of the multi-clamp apparatus of FIGS. 1 and 2 with torque amplifying knobs in a collapsed configuration. The top side view is a mirror image of the bottom side view.
Figure 6:
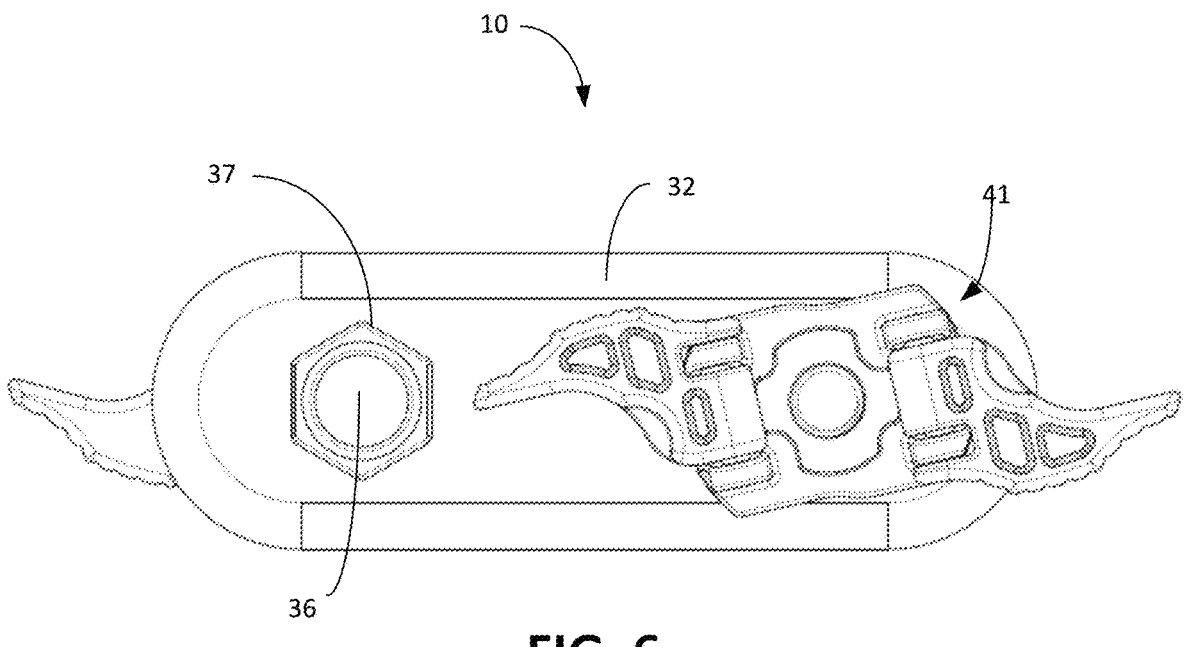
FIG. 6 is a bottom side view of the multi-clamp apparatus of FIGS. 1 and 2 with torque amplifying knobs in an un-collapsed configuration.
Figure 7:
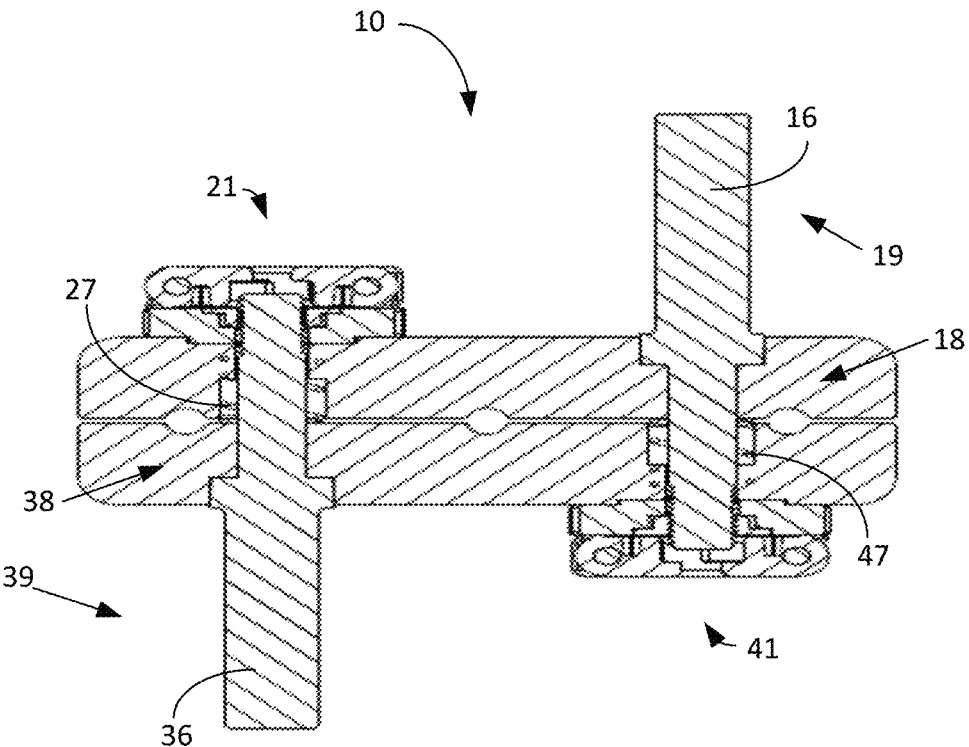
FIG. 7 is a cross-sectional front side view of the multi-clamp apparatus of FIGS. 1 and 2.
Figure 8:
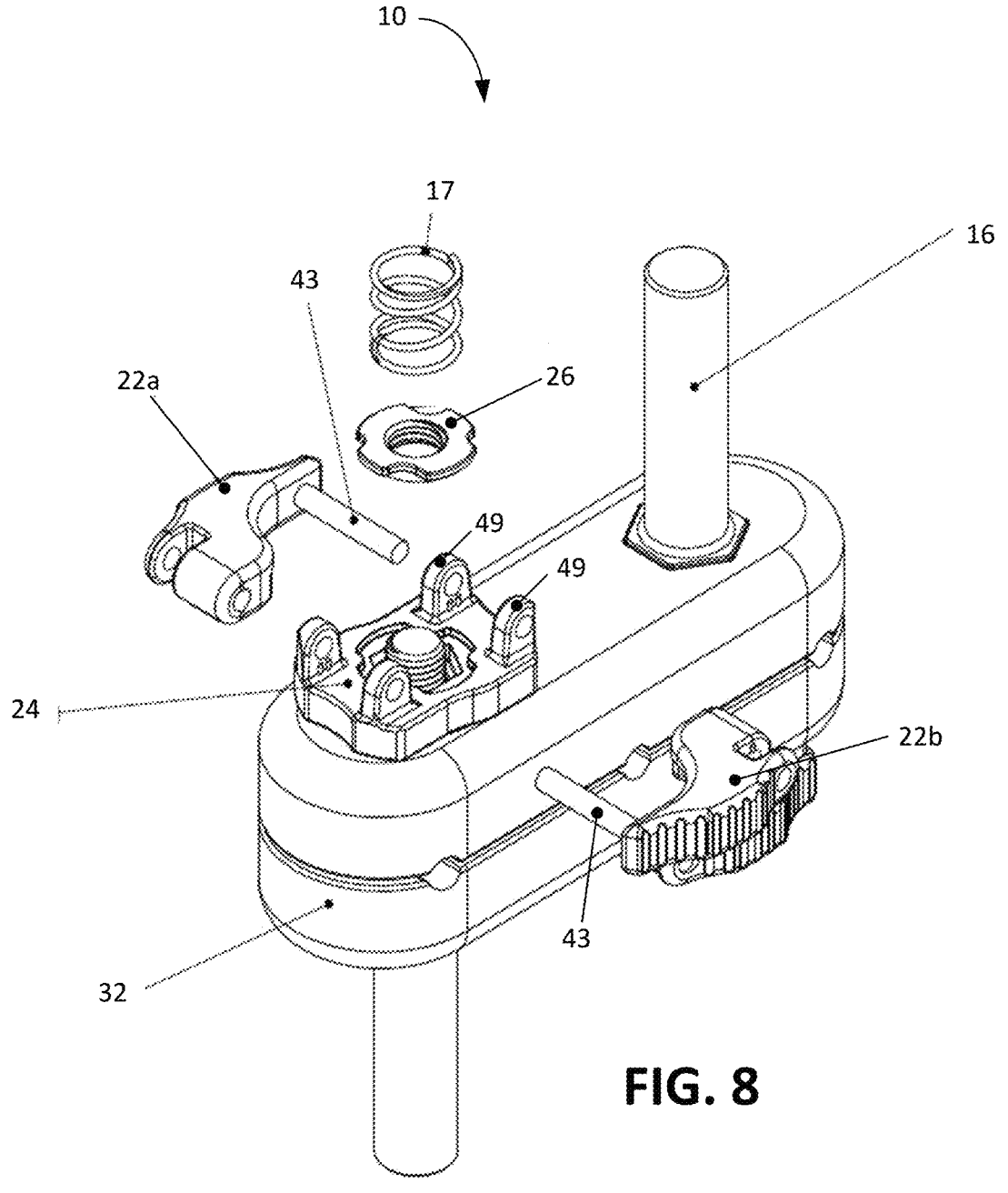
FIG. 8 is an exploded view of the multi-clamp apparatus of FIGS. 1 and 2, showing the various parts of same.

A preferred embodiment, among other possible embodiments, of a multi-clamp apparatus 10 for an orthopedic exterior fixator is shown in FIGS. 1-8. The multi-clamp apparatus 10 has first and second clamp arms 12, 32. Each clamp arm 12, 32 has an elongated longitudinal body extending between first and second ends. Each clamp arm 12, 32 has a plurality (i.e., two or more) of elongated concave crescentic channels, for example, crescentic channels 14a, 14b, 14c and 34a, 34b, 34c, respectively. The concave crescentic channels 14 (i.e., 14a, 14b, 14c) of the first clamp arm 12 face the concave crescentic channels 34

(i.e., 34a, 34b, 34c) of the second clamp arm 32. Each opposing pair of the crescentic channels (i.e., 14a, 34a; 14b, 34b; and 14c, 34c), when aligned together, are of a length, size, and shape to engage and secure a conventional bone pin. Accordingly, three bone pins can be secured and unsecured by this preferred embodiment.

The multi-clamp apparatus 10 further includes a plurality of outrigger bars, for example, first and second cylindrical outrigger bars 16, 36. The outrigger bars 16, 36 can be used for attachment of other fixator components. As examples, one or both of the outrigger bars 16, 36 can be attached to a bone pin or another bar using a clamp, such as the universal clamp described and shown in U.S. Pat. No. 11,660,122. Also, preferably, each outrigger bar 16, 36 has an internal reinforcement with a metallic core to enhance strength and are made from a material that is not subject to an induced current in a magnetic field.

The first and second outrigger bars 16, 36 have first and second cylindrical elongated bodies, respectively, extending between first and second attached ends 18, 38, respectively, and first and second distal ends 19, 39, respectively. The first and second attached ends 18, 38 are attached to the first and second clamp arms 12, 32, respectively. The first and second attached ends 18, 38 each comprise hexagonal first and second collars 17, 37, respectively. The first and second collars 17, 37 reside within respective polygonal recesses, particularly hexagonal recesses, within the first and second clamp arms 12, 32, respectively.

The multi-clamp is equipped with one or more torque amplifying knobs, for example, first and second torque amplifying knobs 21, 41. Each knob 21, 41 has a plurality of collapsible turn levers 22a, 22b and 42a, 42b, respectively. Each turn lever 22 (i.e., 22a, 22b), 42 (i.e., 42a, 42b) has a longitudinal body extending between a movable end and a hinged end. Each knob 21, 41 has a central screw turn actuator 24, 44 with an outer side and an inner side. The hinged end of each turn lever 22, 42 is connected via a hinge 43 to the outer side of the respective central screw turn actuator 24, 44. Each hinge 43 has a pin 47 extending from a corresponding lever and passes through a pair of knuckles 49. The movable end of each turn lever 22, 42 is movable between a collapsed position where each lever 22, 42 is situated over the outer side of the respective central screw turn actuator 24, 44 and an open, un-collapsed position where the movable end is situated outwardly from the outer side of the respective central screw turn actuator 24, 44. When in the collapsed position, the turn levers 22, 42 of each knob 21, 41 can be collapsed in a side-by-side arrangement.

An important feature of the multi-clamp apparatus 10 is that the turn levers 22, 42 are designed ergonomically so that they can be hand operated in the collapsed as well as un-collapsed configurations.

It should be noted that any of the torque amplifying knobs described and/or Illustrated in commonly assigned U.S. Pat. No. 11,660,122, can be implemented on the multi-clamp apparatus 10.

In essence, the first torque amplifying knob 21 prevents and permits movement of the first clamp arm 12 respectively toward and away from the second clamp arm 32, and the second torque amplifying knob 41 prevents and permits movement of the second clamp arm 32 respectively toward and away from the first clamp arm 12.

Each central screw turn actuator 24, 44 is engaged with a respective male threaded screw 25, 45 to permit relative movement of the first and second clamp arms 12, 32 when rotational force is applied to one or both of the knobs 21, 41. In the preferred embodiment, shown in FIGS. 1 through 8, female threaded hexagonal base nuts 26, 46 are situated respectively about the screws 25, 45. In the preferred embodiment, the base nuts 26, 46 are each noncircular around their respective peripheries in that each nut 26, 46 has four equally spaced, outwardly, radially extending nubs that enable the respective actuator 24, 44, which have corresponding apertures to match the nut peripheries, to impose rotational force on the respective nut 26, 46. The central screw turn actuators 24, 44 are designed to rotate the respective nut 26, 46 so that the respective actuators 24, 44 are moved along the respective screw 25, 45.

In other alternative embodiments, one or both of the screw turn actuators 24, 44 can be designed, without the respective base nuts 26, 46, to rotate a head associated with respective screws that are threaded into a nut or other structure in the opposing clamp arm. In yet other alternative embodiments, one or both of the screw turn actuators 24, 44 can be designed with a female threaded part, without the respective base nuts 26, 46, to rotate along the male threaded screws 25, 45.

Each hinge of each knob pivots about a hinge longitudinal body. The hinge longitudinal bodies are parallel, substantially coextensive along the outer side of the respective central screw turn actuator 24, 44, and extend perpendicular to the respective screw 25, 45. The screw axes of screws 25, 45 are generally centered between their respective substantially coextensive hinge longitudinal bodies.

Each of the longitudinal bodies of the turn levers 22, 42 of each knob 21, 41 has inner and outer edges. The inner edges being closer to the respective screw axis of respective screws 25, 45 than the outer edges. The inner edges having respective contours that engage in a mating complimentary manner when the turn levers are collapsed in the side-by-side arrangement. Moreover, the longitudinal bodies have sufficient size to cover a substantial part of the outer side of the respective central screw turn actuator 24, 44 when the respective turn levers 22, 42 are collapsed.

The multi-clamp apparatus 10 can be viewed as having size changeable knobs 21, 41. Each knob 21, 41 is designed to change between a first size and a second size. The first size has at least a part that extends a greater distance in a direction outwardly from the threaded body of the respective screw 25, 45 as compared to the second size so that a greater rotational torque can be applied relative to the respective screw 25, 45 in connection with the first size as compared to the second size.

In the preferred embodiment of the multi-clamp apparatus 10, the clamp apparatus 10 includes at least one spring that applies constant separation force to separate the first and second clamp arms 12, 32. As an example, FIGS. 1-8 show the multi-clamp apparatus 10 with first and second spiraling compression springs 27, 47. The first and second attached ends 18, 38 of the outrigger bars 16, 36, respectively, extend through the first and second compression springs 27, 47, respectively.

In an alternative embodiment, a pair of screws that are separate from the outrigger bars can be employed to engage the torque amplifying knobs and cause relative movement of the clamp arms 12, 32. In this embodiment, the outrigger bars do not need to have a threaded end and are be secured to a respective arm via any suitable mechanism. Also, the head of each screw can be placed opposite of each knob so that the knob rotates and moves along the threaded shaft or, in the alternative, the screw head can be placed on the same side as the knob so that the knob rotates the screw head. In essence, in this embodiment, the means for relative movement includes an elongated male threaded body and a female threaded part, one of the foregoing of which is rotated in order to cause the relative movement. Moreover, the elongated shaft of each screw would pass through a respective compression spring.

Finally, it should be emphasized that the above-described embodiments or examples of the present invention or parts thereof, particularly, any "preferred" embodiments, are merely possible nonlimiting examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention.

At least the following is claimed:

1. A multi-clamp apparatus for an orthopedic exterior fixator, the multi-clamp apparatus comprising:

first and second clamp arms, each clamp arm having an elongated longitudinal body extending between first and second ends, each clamp arm having a plurality of elongated crescentic channels, the crescentic channels of the first clamp arm opposing the crescentic channels of the second clamp arm, each opposing pair of the crescentic channels, when brought together, being of an adequate length, size, and shape to engage and secure a bone pin;

first and second outrigger bars, the first and second outrigger bars having first and second elongated bodies, respectively, extending between first and second attached ends, respectively, and first and second distal ends, respectively, the first and second attached ends being attached to the first and second clamp arms, respectively; and first and second torque amplifying knobs, each knob having a plurality of collapsible turn levers, each turn lever having a longitudinal body extending between a movable end and a hinged end, each knob having a central screw turn actuator with an outer side and an inner side, the hinged end of each turn lever being connected via a hinge to the outer side of the respective central screw turn actuator, the movable end of each turn lever being movable between a collapsed position where each lever is situated over the outer side of the respective central screw turn actuator and an un-collapsed position where the movable end is situated outwardly from the outer side of the respective central screw turn actuator, each central screw turn actuator being engaged with a respective threaded screw that permits relative movement of the first and second clamp arms when rotational force is applied to at least one of the knobs, each screw extending along a respective screw axis.

2. The apparatus of claim 1, wherein each hinge of each knob pivots about a hinge longitudinal body, the hinge longitudinal bodies being parallel, being substantially coextensive along the outer side of the respective central screw turn actuator, and extending perpendicular to the respective screw axis, the respective screw axis generally centered between the respective substantially coextensive hinge longitudinal bodies;

wherein the turn levers of each knob are collapsed in a side-by-side arrangement; and wherein each of the longitudinal bodies of the turn levers of each knob have inner and outer edges, the inner edges being closer to the screw axis than the outer edges, the inner edges having respective contours that engage in a mating complimentary manner when the turn levers are collapsed in the side-by-side arrangement, the longitudinal bodies having sufficient size to cover a substantial part of the outer side of the respective central screw turn actuator when the respective turn levers are collapsed.

3. The apparatus of claim 1, wherein each of the first and second attached ends of the first and second outrigger bars comprises one of the respective screws that is engaged with one of the respective central screw turn actuators.

4. The apparatus of claim 3, wherein the first and second attached ends comprise hexagonal first and second collars respectively, the first and second collars residing within respective hexagonal recesses within the first and second clamp arms, respectively.

5. The apparatus of claim 1, wherein the first knob prevents and permits movement of the first clamp arm toward and away from the second clamp arm and the second knob prevents and permits movement of the second clamp arm toward and away from the first clamp arm.

6. The apparatus of claim 1, further comprising at least one spring that applies a force to separate the first and second clamp arms.

7. The apparatus of claim 1, further comprising first and second compression springs and wherein the first and second attached ends extend through the first and second compression springs, respectively.

8. A multi-clamp apparatus for an orthopedic exterior fixator, the multi-clamp apparatus comprising:

first and second clamp arms, each clamp arm having an elongated longitudinal body extending between first and second ends, each clamp arm having a plurality of crescentic channels, the crescentic channels of the first clamp arm opposing the crescentic channels of the second clamp arm;

first and second outrigger bars, each outrigger bar having an elongated body extending between an attached end and a distal end, the attached ends being attached to the first and second clamp arms, respectively; and first and second size changeable knobs, each knob designed to change between a first size and a second size, the first size having at least a part that extends a greater distance in a direction outwardly from a threaded body of the respective screw as compared to the second size so that a greater rotational torque can be applied relative to the respective screw in connection with the first size as compared to the second size, each knob having a central screw turn actuator engaged with the respective threaded screw that permits relative movement of the first and second clamp arms when rotational force is applied to at least one of the knobs, each screw extending along a respective screw axis; and wherein each size changeable knob includes at least one collapsible turn lever, each turn lever having a longitudinal body extending between a movable end and a hinged end, each central screw turn actuator having an outer side and an inner side, the hinged ends of each turn lever being connected via respective hinges to the outer sides of the respective central screw turn actuators, the movable ends of each turn lever being movable between a collapsed position where the movable ends are situated over the outer side of the respective central screw turn actuator and an un-collapsed position where the movable ends are situated outwardly from the outer sides of the respective central screw turn actuator.

9. The apparatus of claim 8, wherein each hinge of each knob pivots about a hinge longitudinal body, the hinge longitudinal body extending perpendicular to the respective screw;

wherein an axis that is perpendicular to and extends through the screw axis also extends through a central part of the hinge longitudinal body of each hinge; and wherein each longitudinal body of each turn lever has inner and outer edges, the inner edge being closer to the screw axis than the outer edge, the longitudinal body having sufficient size to cover a substantial part of the outer side of the central screw turn actuator when the at least one turn lever is collapsed.

10. The apparatus of claim 8 wherein each of the first and second attached ends of the first and second outrigger bars comprises one of the respective screws that is engaged with one of the respective central screw turn actuators.

11. The apparatus of claim 10, wherein the first and second attached ends comprise hexagonal first and second collars respectively, the first and second collars residing within respective hexagonal recesses within the first and second clamp arms, respectively.

12. The apparatus of claim 8, wherein the first knob prevents and permits movement of the first clamp arm toward and away from the second clamp arm and the second knob prevents and permits movement of the second clamp arm toward and away from the first clamp arm.

13. The apparatus of claim 8, further comprising at least one spring that applies a force to separate the first and second clamp arms.

14. The apparatus of claim 8, further comprising first and second compression springs and wherein the first and second attached ends extend through the first and second compression springs, respectively.

15. A multi-clamp apparatus for an orthopedic exterior fixator, the multi-clamp apparatus comprising:

first and second clamp arms, each clamp arm having an elongated longitudinal body extending between first and second ends, each clamp arm having a plurality of elongated crescentic channels, the crescentic channels of the first clamp arm opposing the crescentic channels of the second clamp arm, each opposing pair of the crescentic channels, when brought together, being of an adequate length, size, and shape to engage and secure a bone pin;

first and second outrigger bars, the first and second outrigger bars having first and second elongated bodies, respectively, extending between first and second attached ends, respectively, and first and second distal ends, respectively, the first and second attached ends being attached to the first and second clamp arms, respectively; and first and second torque amplifying knobs, each knob having a plurality of collapsible turn levers, each turn lever having a longitudinal body extending between a movable end and a hinged end, each knob having a central screw turn actuator with an outer side and an inner side, the hinged end of each turn lever being connected via a hinge to the outer side of the respective central screw turn actuator, the movable end of each turn lever being movable between a collapsed position where each lever is situated over the outer side of the respective central screw turn actuator and an un-collapsed position where the movable end is situated outwardly from the outer side of the respective central screw turn actuator, each central screw turn actuator being engaged with a respective means for causing relative movement of the first and second clamp arms when rotational force is applied to the respective knob.

16. The apparatus of claim 15, wherein the means for causing comprises a respective elongated male threaded body and a respective female threaded part, one of the foregoing of which is rotated in order to cause the relative movement of the first and second clamp arms.

17. The apparatus of claim 16, wherein the first and second outrigger bars include the respective elongated threaded body and the central screw turn actuators include the respective female threaded part.

18. The apparatus of claim 15, further comprising at least one spring that applies a force to separate the first and second clamp arms.

19. The apparatus of claim 15, wherein the means for causing comprises:

a first elongated male threaded body with a respective first female threaded part, one of the foregoing of which is rotated in order to cause the relative movement of the first and second clamp arms;

a second elongated male threaded body with a respective second female threaded part, one of the foregoing of which is rotated in order to cause the relative movement of the first and second clamp arms; and further comprising first and second compression springs, the first and second elongated male threaded bodies extending through the first and second compression springs, respectively.

20. The apparatus of claim 15, wherein the first knob prevents and permits movement of the first clamp arm toward and away from the second clamp arm and the second knob prevents and permits movement of the second clamp arm toward and away from the first clamp arm.

* * * * *